United States Patent

Xie et al.

(10) Patent No.: US 9,494,532 B2
(45) Date of Patent: Nov. 15, 2016

(54) SYSTEM AND METHOD FOR SIDE-BY-SIDE INSPECTION OF A DEVICE

(75) Inventors: Binglong Xie, Lawrenceville, NJ (US); Yakup Genc, Dayton, NJ (US); Xiang Gao, Skillman, NJ (US)

(73) Assignee: Siemens Energy, Inc., Orlando, FL (US)

( * ) Notice: Subject to any disclaimer, the term of this patent is extended or adjusted under 35 U.S.C. 154(b) by 841 days.

(21) Appl. No.: 13/240,632

(22) Filed: Sep. 22, 2011

(65) Prior Publication Data

US 2012/0154594 A1 Jun. 21, 2012

Related U.S. Application Data

(60) Provisional application No. 61/386,092, filed on Sep. 24, 2010.

(51) Int. Cl.
| | |
|---|---|
| *G01N 21/95* | (2006.01) |
| *G01B 11/245* | (2006.01) |
| *G01N 21/954* | (2006.01) |
| *G06T 7/00* | (2006.01) |

(52) U.S. Cl.
CPC ......... *G01N 21/9515* (2013.01); *G01B 11/245* (2013.01); *G01N 21/954* (2013.01); *G06T 7/001* (2013.01); *G06T 2200/24* (2013.01); *G06T 2207/30164* (2013.01)

(58) Field of Classification Search
CPC ... G06T 7/001; G06T 7/0002; G06T 7/0004; G06T 7/2093; G01B 11/24; G01B 11/022; G01N 21/9515; G01N 21/958
See application file for complete search history.

(56) References Cited

U.S. PATENT DOCUMENTS

| | | | |
|---|---|---|---|
| 4,742,227 A | 5/1988 | Takenaka | |
| 4,811,091 A | 3/1989 | Morrison et al. | |
| 5,255,096 A | 10/1993 | Boyle | |
| 5,307,447 A | 4/1994 | Asano et al. | |
| 6,151,063 A * | 11/2000 | Nishikawa | 348/92 |
| 6,487,922 B1 | 12/2002 | Bauer et al. | |

(Continued)

FOREIGN PATENT DOCUMENTS

| | | |
|---|---|---|
| EP | 0593183 A2 | 4/1994 |
| JP | H06148093 A | 5/1994 |
| JP | H07225121 A | 8/1995 |
| JP | S639850 A | 1/1998 |
| JP | 2007527993 A | 10/2007 |
| JP | 2008020426 A | 1/2008 |

OTHER PUBLICATIONS

Japanese Office Action and Translation dispatched Feb. 18, 2014 corresponding to Japanese Application No. 20123-530338 filed Sep. 23, 2011 (14 pages).

*Primary Examiner* — Geepy Pe

(57) ABSTRACT

Systems and methods for inspecting a device include arranging the device in a known position relative to a plurality of movable cameras mounted on a controllable actuator controlled by a computing device and pointed at the device by controlling the controllable actuator to position a camera with a user interface on the computing device with a display, and the display displays a virtual image from the camera into CAD model of the device and an image of the device generated by the camera in a side-by-side or in an overlay fashion or both.

18 Claims, 3 Drawing Sheets

(56) References Cited

U.S. PATENT DOCUMENTS

| | | |
|---|---|---|
| 6,580,971 B2 | 6/2003 | Bunn et al. |
| 7,075,296 B2 | 7/2006 | Moore |
| 8,159,243 B2 * | 4/2012 | Portune .................... 324/750.23 |
| 2005/0147290 A1 * | 7/2005 | Ong et al. ..................... 382/152 |
| 2005/0196040 A1 * | 9/2005 | Ohara ........................... 382/167 |
| 2006/0140473 A1 | 6/2006 | Brooksby et al. |
| 2008/0084481 A1 | 4/2008 | Lindsay |

* cited by examiner

US 9,494,532 B2

SYSTEM AND METHOD FOR SIDE-BY-SIDE INSPECTION OF A DEVICE

STATEMENT OF RELATED CASES

This application claims priority to and the benefit of U.S. Provisional Patent Application No. 61/386,092 filed on Sep. 24, 2010.

TECHNICAL FIELD

The present invention relates to inspection systems and methods that use cameras.

BACKGROUND

For industrial devices and equipment, computerized inspection from camera images provides very accurate information. However, if the object being inspected is complex (for example a modern gas turbine machine), and when multiple cameras and multiple configurations of cameras are involved, inspection becomes difficult. It is often not intuitive to figure out the spatial relationship between each camera or camera configuration and the inspected device. This hampers the productivity of inspection.

The inspection process is particularly difficult when the device being inspected is complex. For example, the inspection of a modern gas turbine machine with existing inspection systems and methodology creates difficulties. One reason for this is because the devices are large and have complex shapes which can be difficult to locate when examining a video feed of the inspection.

Accordingly, new and improved systems and methodologies for inspecting complex devices are needed.

SUMMARY

The present invention provides direct support to let an inspector inspecting a device be aware of the exact situation of the camera configuration with respect of the device being inspected. In accordance with one aspect of the present invention, cameras are installed on an actuator which can be controlled from the computer with user interface devices including joysticks, keyboard and mouse. The cameras can have multiple degrees of freedom. Software in a computing device fully controls the actuators and knows the spatial location and orientation of each camera.

A CAD model of the inspected object is available, and loaded to software on a computing device. The video images from the cameras are transferred live to the computer. With the information available above, the system of the present invention can selectively present side by side: Live images from cameras; a virtual view of the camera into the CAD model and a scene overview of the cameras and the CAD model, with live images overlaid on the CAD model.

With such views, an inspector will exactly know where the cameras are with respect to the inspected device, what the views look like without turning on the camera video, and what the real images from the camera are, all in the same application at the same time. This will greatly help the user to create predefined configurations, carry out training, and perform practical inspection.

Thus, new and improved methods and systems for inspecting a device are provided in accordance with various aspects of the present invention.

In accordance with one aspect of the present invention, a method for inspecting a device is provided. The device being inspected is arranged in a known position relative to a plurality of movable cameras, the plurality of movable cameras being mounted on a controllable actuator. Then the actuator is moved to point the plurality of cameras at the device. The controllable actuator is controlled by the inspector/user to position the camera by means of a user interface.

A computing device accesses a CAD model of the device being inspected and renders a virtual image of the device being inspected from the CAD model.

Then, an image of the device being inspected is generated by the camera (or cameras) on a display. The computing device also causes the rendered virtual image of the device to be displayed on the display.

In accordance with one aspect of the present invention, the image of the device generated by the camera and the rendered virtual image from the CAD model are displayed side by side on the display.

In accordance with another aspect of the present invention, the image of the device generated by the camera and the rendered virtual image from the CAD model are also displayed in an overlay manner with the image overlaid on the rendered virtual image such that the image is properly located on the rendered virtual image of the CAD model.

In accordance with another aspect of the present invention, one or more additional images from the plurality of cameras are displayed in an overlay manner with the plurality of images overlaid on the rendered virtual image such that each of the plurality of images is properly located on the rendered virtual image of the CAD model.

In accordance with another aspect of the present invention, the device can be inspected after the images of the device have been taken. In this case, the images are taken by cameras and then stored for analysis in accordance with aspects of the present invention.

In accordance with this aspect of the invention, a computing device retrieves an image of the device, a plurality of physical characteristics of a camera generating the image, a location and orientation of the camera and a calibration of the device to the camera. The computing device also retrieves a CAD model of the device being inspected.

The computing device renders a virtual image of the device from the CAD model of the device. The computing device can render a part of the CAD model or all of it, depending on the section of the device being interested.

The computing device then causes the image of the device and a corresponding section of the virtual image of the device to be simultaneously displayed. The image of the device generated by the camera and the rendered virtual image from the CAD model can be displayed side by side on the display. Additionally, the image of the device generated by the camera and the rendered virtual image from the CAD model can be displayed in an overlay manner with the image overlaid on the rendered virtual image such that the image is properly located on the rendered virtual image of the CAD model.

One or more additional images from the plurality of cameras can be displayed in an overlay manner with the plurality of images overlaid on the rendered virtual image such that each of the plurality of images is properly located on the rendered virtual image of the CAD model.

Systems to perform the above described methods and other methods described herein are also provided in accordance with aspects of the present invention. In accordance with one aspect of the present invention, an inspection system for inspecting a device includes a plurality of cameras, each of the plurality of cameras being mounted on a controllable actuator and being pointed at the device. It also includes a CAD model of the device stored in memory accessible by a computing device. The computing device renders a virtual image of at least a section of the device being inspected. The system includes at least one display connected to the plurality of cameras to display an image from one or more of the plurality of cameras.

The computing device is connected to each controllable actuator and to the at least one display and includes a user interface to control each controllable actuator. The computing device also causes the rendered virtual image to be displayed on the at least one display.

DRAWINGS

DESCRIPTION

Figure 1:
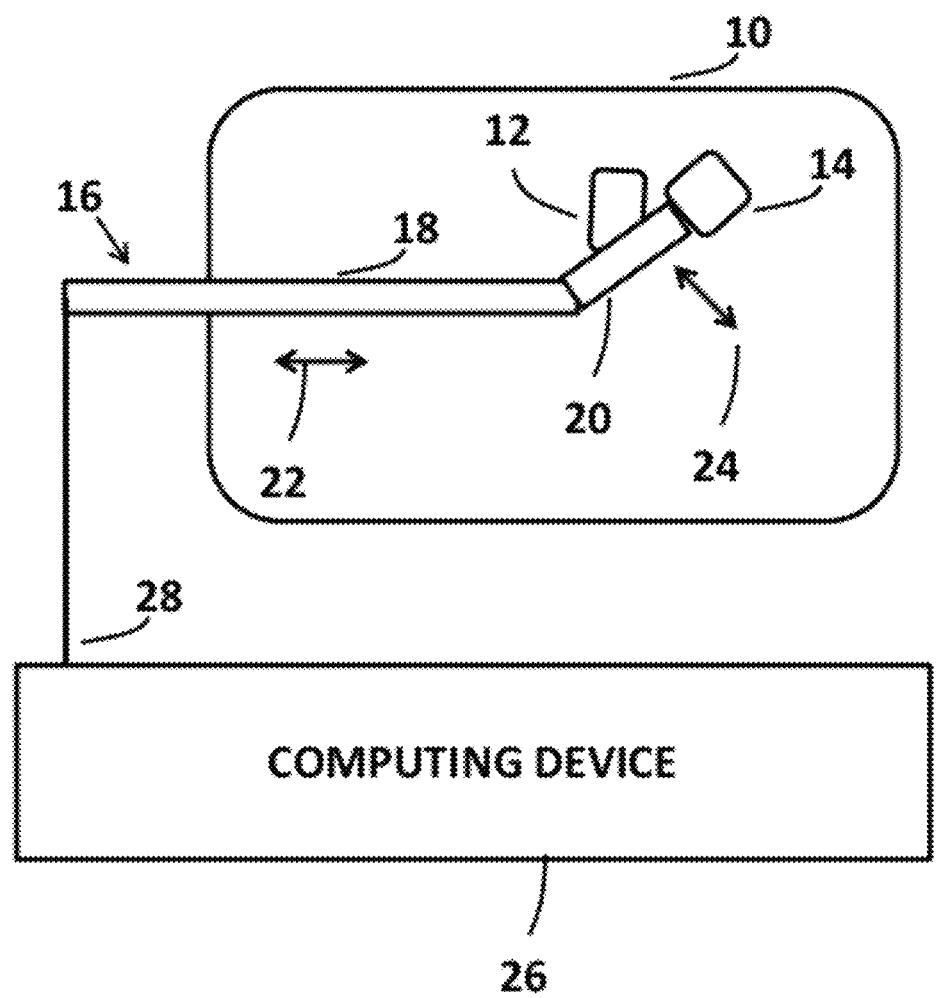
FIG. 1 illustrates a system for inspecting a device in accordance with an aspect of the present invention.

FIG. 1 illustrates a device being inspected and an inspection system in accordance with an aspect of the present invention. A device 10 being inspected is illustrated. The device 10 can be any of a large number of devices, including turbines, gas turbines and the like. The devices being inspected can be quite complex, both in size and in shape. When using a amera to do the inspection, it is quite easy to lose track of where a defect is located. The defects can include scars, cracks, stains and other defects.

A plurality of cameras 12 and 14 is moved inside the device 10 being inspected to conduct the inspection. The cameras 12 and 14 are mounted on a movable, controllable actuator 16. In accordance with an aspect of the present invention, the actuator 16 includes a first arm 18 and a second arm 20.

Although two cameras 12 and 14 are illustrated, a single camera can be used. Alternatively, more than two cameras can also be used.

The first arm 18 can be controllable moved along the direction indicated by arrow 22. Thus, the cameras 12 and 14 can be moved through the center of the device 10 being inspected to perform the inspection.

The second arm 20 can be rotated in the direction indicated by arrow 24. The second arm 20 can also be rotated in and out of the figure. Thus, the controllable movable actuator 16 has multiple degrees of freedom. As the actuator 16 is moved along direction 22, the second arm 20 can be rotated to examine all internal sections of the device 10 being inspected.

In accordance with another aspect of the present invention, a transmission circuit is attached to the actuator 16 to communicate the actuator 16 position and orientation to a computing device 26 via the interface 28. The transmission circuit can also transmit all of the physical characteristics of the cameras 12 and 14 to the computing device 26. In this way, the computing device 26 knows what the cameras 12 and 14 are looking at on the device 10 and the computing device 26 understands the characteristics of the cameras 12 and 14.

Figure 2:
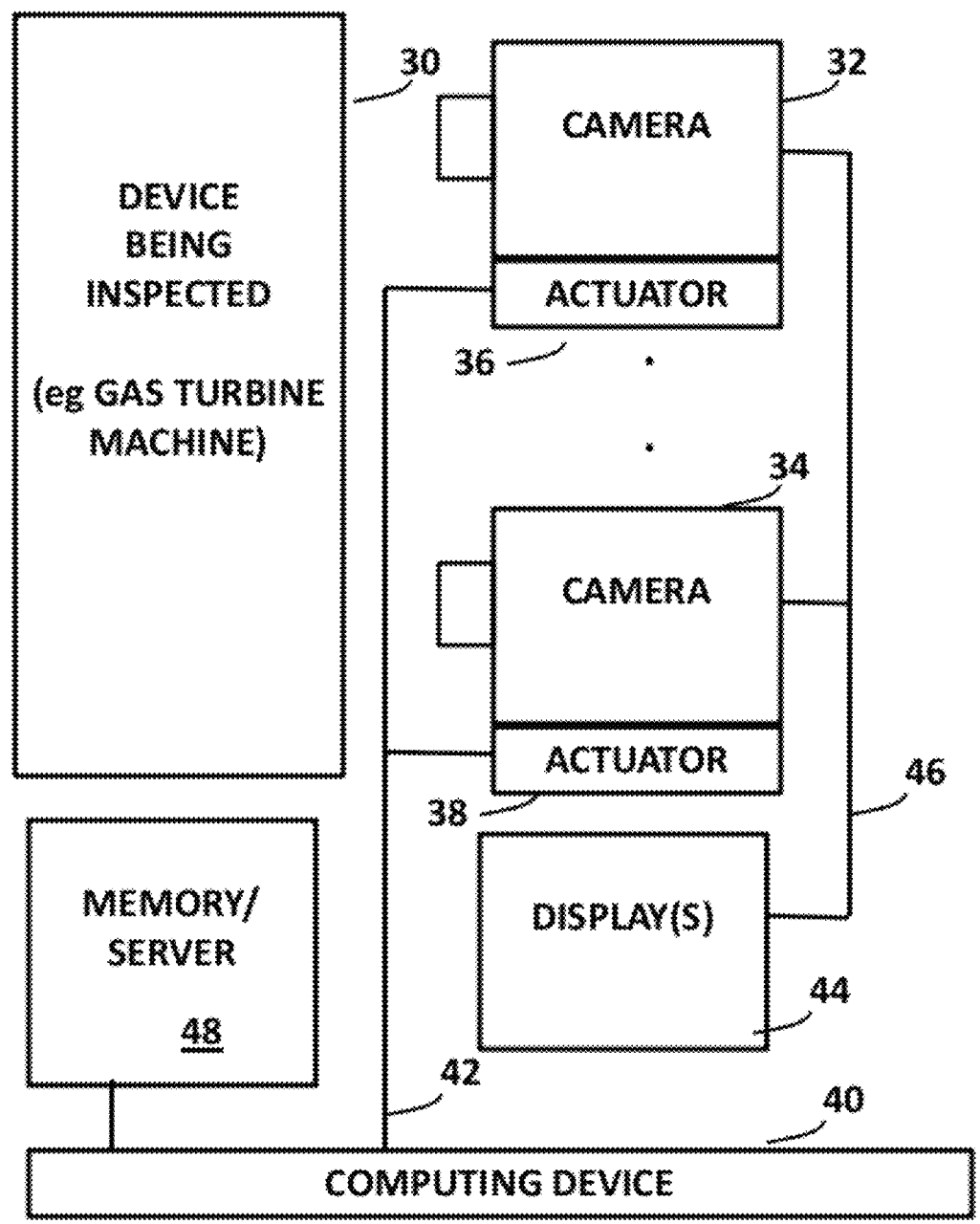
FIG. 2 illustrates position data of an actuator that is displayed by a computing device on the display.

The system for inspecting devices in accordance with an aspect of the present invention is further illustrated in FIG. 2. A device 30 that is to be inspected is illustrated. The device is typically a complex device, such as a gas turbine machine.

The system includes a plurality of cameras 32 and 34. As before, although two cameras are shown, more than two cameras can be utilized. In accordance with other aspects of the present invention, a single camera can be used. The types of cameras used are standard industry cameras used to perform inspection of complex device.

Each of the cameras 32 and 34 are attached to an actuator 36 and 38, respectively. In accordance with an aspect of the invention, the actuators 36 and 38 are part of a single structure that includes multiple parts. Alternatively, each actuator can 36 and 38 can be individual actuator structures. The actuators 36 and 38 provide multiple degrees of freedom for each of the plurality of cameras 32 and 34. This way, the cameras 32 and 34 can be pointed at any desired location on the device being inspected.

The actuators can be controlled by a computing device 40 through an interface 42. The computing device can be any type of computing device, including a personal computer, a laptop or even a specially designed computer. The position and orientation of the actuators 36 and 38 relative to the device being inspected are controlled by a user interface that is part of the computing device 20. User interfaces that can be used include a mouse, a keyboard, a keypad, a touch screen and a joystick. These are provided as part of the computing device.

The system includes one or more displays 44 connected to each of the plurality of cameras 32 and 34. In one embodiment of the present invention, each of the cameras 32 and 34 are connected to a display 44. In accordance with another aspect of the present invention, one camera can be individually connected to one display.

One or more CAD models of a plurality of devices that can be inspected are stored in a memory 48. The memory 48 can be part of a remote server that is accessed by the computing device 40 in a remote manner. The memory 48 includes a CAD model of the device 30 being inspected.

The computing device 40 renders a virtual image of the device being inspected from the CAD model of the device being inspected. This can be performed using publicly available software, such as openGL. The computing device 40 can render a complete virtual image of the entire device being inspected or can render a virtual image of sections of the device being inspected to save time.

The position and orientation of the cameras 32 and 34 are controlled from a user interface on the computing device 40 to obtain images of the device being inspected. In accordance with an aspect of the present invention, the images from the device being inspected and the rendered virtual image are displayed simultaneously.

Figure 3:
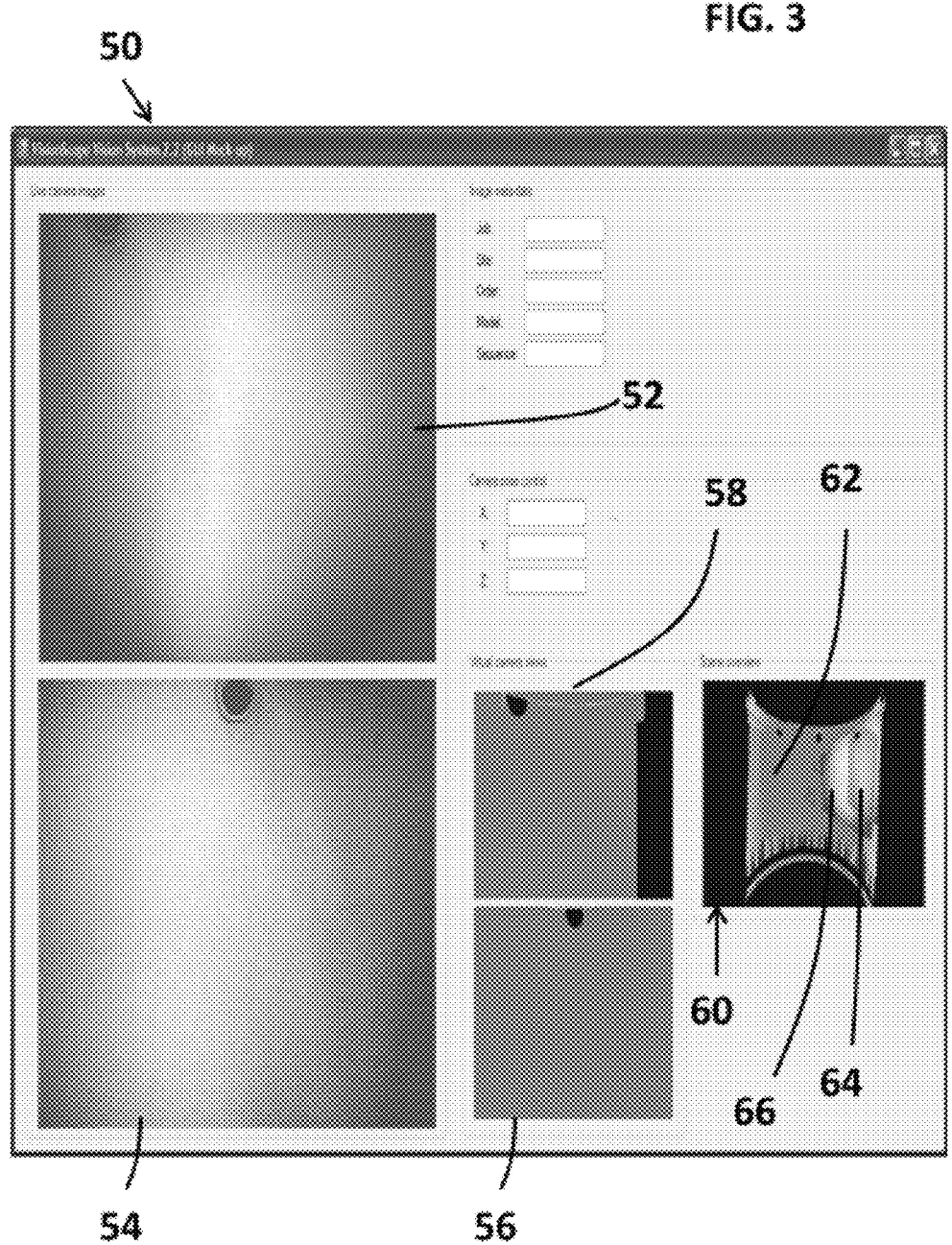
FIG. 3 illustrates a window that the computing device displays on the display in accordance with an aspect of the present invention.

FIG. 3 illustrates a window 50 displayed by the computing device 40. Images 50 and 52 are live images from the device being inspected. If there are defects, such as scars, cracks, decoloration, etc., those defects would appear here. However, simply examining these images may leave the inspector uncertain about their positions in the device being inspected. The inspector may also be uncertain about the nature of the device being inspected and whether there is in fact a defect.

Thus, the present invention also displays rendered virtual images related to the live images as images 58 and 56. Thus, live image 52 is related to rendered virtual image 58. Also, live image 54 is related to rendered virtual image 56.

In general, the virtual images are rendered from the CAD model with given virtual camera positions and internal characteristics. To establish the correlation between the virtual image and live image, the virtual camera must have the same position and internal characteristics as the live camera. An internal calibration process estimates the internal characteristics of the live camera. After an external calibration process, the position of the live camera regarding to the CAD model at any time is calculated from the actuator positional readings.

Once the positional and internal parameters of the live cameras are obtained, they are used by the virtual cameras to render from CAD model the virtual image 56 or 58 using computer graphics technologies such as OpenGL. The virtual image and live image show similar structures, such as the hole at the top center of live image 54 and virtual image 56.

Thus, aspects of the present invention allow a live image of a device being inspected to be displayed with a rendered virtual image. In accordance with an aspect of the invention, the live image 54 is displayed adjacent the rendered virtual image 56. The images can be displayed side by side. This allows defects in the device under inspection to be more readily identified because the inspector can view a model of the device in its unused state while examining an image of the device being inspected that has been used.

Additionally or alternatively, the live video image 52 can be overlaid as image 64 on a larger version of the rendered virtual image 62 in a window 60. This is done by correlating the position The computing device knows the position and orientation of the cameras because the actuator reports its position to the computing device. Also, the needed physical characteristics of the cameras can be transmitted through the actuator interface to the computing device. Alternatively, the physical characteristics of the cameras can be stored in memory and accessed by the computing device as needed. The computing device uses this information to locate the live images 64 and 66 on the rendered virtual image 62.

As shown in FIG. 3, multiple images 64 and 66 can be overlaid on the rendered virtual image 62 of the device under inspection.

The display 60 helps the inspector to readily identify the location of the image and of any defect located in the live images 52 and 54.

The inspection station of the present invention can be used in different modes. In a first mode, live images, generating from a real time inspection of the device being inspected are fed to the computing device. In this case, the computing device performs the steps described above in real time and can be used to control the location of the actuators and therefore the cameras.

In accordance with another aspect of the present invention, the images of the device can be generated using the cameras and movable controllable actuators and those images stored in a memory. When time for analysis comes, the images are stored in a memory accessible by the computing device.

The computing device, as before, has access to a CAD model of the device being inspected. The computing device renders a virtual image of the device being inspected from the CAD model using, for example, openGL. The computing device then causes one or more of the live images to be displayed simultaneously with the rendered virtual image.

The display of the live images and the rendered virtual image are either side-by-side or in an overlay manner as described above or both. The side by side display and the overlay display are shown in FIG. 3.

The device being inspected is arranged in a known location to the cameras/actuators prior to the inspection. This allows the computing device to relate the images to an appropriate section of the CAD model of the device. This is referred to as calibration. The calibration can be performed manually and the details of the calibration reported to the computing device.

While there have been shown, described and pointed out fundamental novel features of the invention as applied to preferred embodiments thereof, it will be understood that various omissions and substitutions and changes in the form and details of the methods and systems illustrated and in its operation may be made by those skilled in the art without departing from the spirit of the invention. It is the intention, therefore, to be limited only as indicated by the scope of the claims.

The invention claimed is:

1. A method for inspection, comprising:
one or more users arranging a plurality of movable cameras in a known position relative to a gas turbine machine, the plurality of movable cameras being mounted on a controllable actuator having a first arm and a second arm, the controllable actuator being controlled by a computing device, the first arm being enabled to move linearly inside the gas turbine machine, the second arm attached to the first arm being enabled to be rotated relative to the first arm in two perpendicular planes, the second arm supporting one of the plurality of movable cameras enabled to be placed in a plurality of positions inside the gas turbine machine;
the computing device retrieving a Computer-Aided-Design (CAD) model of the gas turbine machine to be inspected;
the computing device pointing the one of the plurality of movable cameras at the inside of the gas turbine machine;
the computing device controlling the controllable actuator to position the one of the plurality of movable cameras at a first position with a user interface on the computing device;
the computing device rendering an inside image from a virtual view of the one of the plurality of movable cameras in the first position into the CAD model of the gas turbine machine with the computing device;
the computing device displaying an image of the gas turbine machine generated by the one of the plurality of movable cameras in the first position, which is an image of the gas turbine machine in a used state, on a display;
the computing device causing the image from the virtual view of the one of the plurality of movable cameras in the first position into the CAD model of the gas turbine machine, which is an inside image of the gas turbine machine in an unused state, to be displayed on the display; and
the computer device performing inspection using the CAD model of the gas turbine machine and the image both displayed simultaneously on the display.

2. The method of claim 1, wherein the image of the gas turbine machine generated by the one of the plurality of movable cameras in the first position and the image from the virtual view of the one of the plurality of movable cameras in the first position into the computer CAD model of the gas turbine machine are both displayed simultaneously on the display.

3. The method of claim 1, wherein the image of the gas turbine machine generated by the one of the plurality of movable cameras in the first position and the image from the virtual view of the one of the plurality of movable cameras in the first position into the computer CAD model of the gas turbine machine are displayed in an overlay manner with the image of the gas turbine machine generated by the one of the plurality of movable cameras in the first position overlaid on the image from the virtual view of the one of the plurality of movable cameras in the first position into the CAD model of the gas turbine machine.

4. The method of claim 3, wherein one or more additional images generated by the plurality of movable cameras are displayed in an overlay manner with the one or more additional images being overlaid on the image from the virtual view of the one of the plurality of movable cameras in the first position into the CAD model of the gas turbine machine.

5. The method of claim 3, wherein the computing device processes the image generated by the one of the plurality of movable cameras in the first position and the image from the virtual view of the one of the plurality of movable cameras in the first position into the CAD model of the gas turbine machine in accordance with a location and an orientation of the controllable actuator and in accordance with physical characteristics of the one of the plurality of movable cameras when displaying the image generated by the one of the plurality of movable cameras in the first position and the image from the virtual view of the one of the plurality of movable cameras in the first position into the CAD model of the gas turbine machine for inspection.

6. The method of claim 3, wherein the controllable actuator can move with multiple degrees of freedom.

7. The method of claim 6, wherein the controllable actuator reports a position and an orientation to the computing device and the computing device uses the position and the orientation as well as information concerning physical characteristics of the one of the plurality of movable cameras to render the image from the virtual view of the one of the plurality of movable cameras in the first position into the CAD model of the gas turbine machine.

8. A method for inspection, comprising:
a computing device obtaining an image of an inside of a gas turbine machine generated by a camera in a known position inside the gas turbine machine, a plurality of physical characteristics of the camera generating the image of the inside of the gas turbine machine, a location and an orientation of the camera in the known position and a calibration of the gas turbine machine to the camera and controlling the location and the orientation of the camera selected from a plurality of locations and orientations with a user interface on the computing device;
the computing device retrieving a Computer-Aided-Design (CAD) model of the gas turbine machine;
the computing device rendering an inside image from a virtual view of the camera in the known position into the CAD model of the gas turbine machine;
the computing device causing the image of the inside of the gas turbine machine generated by the camera in the known position and a corresponding section of the image from the virtual view of the camera in the known position into the CAD model of the gas turbine machine to be simultaneously displayed on a display, wherein the CAD model represents an unused state of the gas turbine machine and the image of the inside of the gas turbine machine represents a used state of the gas turbine machine; and
the computer device performing inspection using the CAD model of the gas turbine machine and the image both displayed simultaneously on the display.

9. The method of claim 8, wherein the image of the inside of the gas turbine machine generated by the camera in the known position and the image from the virtual view of the camera in the known position into the CAD model of the gas turbine machine are displayed side by side on the display.

10. The method of claim 8, wherein the image of the inside of the gas turbine machine generated by the camera in the known position and the image from the virtual view of the camera in the known position into the CAD model of the gas turbine machine are displayed in an overlay manner with the image of the inside of the gas turbine machine overlaid on the image from the virtual view of the camera in the known position into the CAD model of the gas turbine machine for inspection.

11. The method of claim 10, wherein one or more additional images of the gas turbine machine are displayed in an overlay manner with the one or more additional images overlaid on the image from the virtual view of the camera in the known position into the CAD model of the gas turbine machine.

12. The method of claim 10, wherein the computing device processes the image of the inside of the gas turbine machine and the image from the virtual view of the camera into the CAD model of the gas turbine machine in accordance with the location and the orientation of the camera and in accordance with physical characteristics of the camera.

13. An inspection system, comprising:
a plurality of cameras, each of the plurality of cameras being mounted on a controllable actuator under control of a computing device and being pointed at an inside of a gas turbine machine to be inspected;
a Computer-Aided-Design (CAD) model of the gas turbine machine stored in memory accessible by the computing device, wherein the computing device renders an image from a virtual view of one of the plurality of cameras into the CAD model of at least a section of the gas turbine machine being inspected;
at least one display connected to the plurality of cameras to display an image of the inside of the gas turbine machine generated by the one of the plurality of cameras, and the CAD model of the gas turbine machine simultaneously; and
the computing device connected to the controllable actuator and to the at least one display, the computing device including a user interface to control the controllable actuator, and to perform inspection using the image of the inside of the gas turbine machine generated by the one of the plurality of cameras and the CAD model of the gas turbine machine both displayed simultaneously on the at least one display.

14. The inspection system of claim 13, wherein the image of the inside of the gas turbine machine generated by the one of the plurality of cameras and the image from the virtual view of the one of the plurality of cameras into the CAD model of the gas turbine machine are displayed side by side on the at least one display.

15. The inspection system of claim 13, wherein the image of the inside of the gas turbine machine generated by the one of the plurality of cameras and the image from the virtual view of the one of the plurality of cameras into the CAD model of the gas turbine machine are displayed in an overlay manner.

16. The inspection system of claim 15, wherein one or more additional images generated by the plurality of cameras are displayed in an overlay manner on the image from the virtual view of the one of the plurality of cameras into the CAD model of the gas turbine machine.

17. The inspection system of claim 13, wherein the controllable actuator can move with multiple degrees of freedom.

18. The inspection system of claim 17, wherein the controllable actuator reports a position and an orientation to the computing device and the computing device uses the position and the orientation as well as information concerning physical characteristics of the one of the plurality of cameras to render the image from the virtual view of the one of the plurality of cameras into the CAD model of the gas turbine machine for inspection.

* * * * *